United States Patent
Lee et al.

(10) Patent No.: US 12,310,886 B2
(45) Date of Patent: May 27, 2025

(54) OPHTHALMIC DEVICES, SYSTEMS AND METHODS FOR TREATING DRY EYE

(71) Applicant: Verily Life Sciences LLC, Dallas, TX (US)

(72) Inventors: Fred Shungneng Lee, South San Francisco, CA (US); Dimitri Azar, South San Francisco, CA (US)

(73) Assignee: Verily Life Sciences LLC, Dallas, TX (US)

( * ) Notice: Subject to any disclaimer, the term of this patent is extended or adjusted under 35 U.S.C. 154(b) by 919 days.

(21) Appl. No.: 17/391,835

(22) Filed: Aug. 2, 2021

(65) Prior Publication Data

US 2022/0031506 A1 Feb. 3, 2022

Related U.S. Application Data

(60) Provisional application No. 63/060,363, filed on Aug. 3, 2020.

(51) Int. Cl.
*A61F 9/00* (2006.01)
*A61B 5/00* (2006.01)
(Continued)

(52) U.S. Cl.
CPC .......... *A61F 9/0017* (2013.01); *A61B 5/4836* (2013.01); *A61B 5/6821* (2013.01);
(Continued)

(58) Field of Classification Search
CPC ........ A61F 9/0017; A61F 9/00; A61B 5/4836; A61B 5/6821; A61B 5/1103;
(Continued)

(56) References Cited

U.S. PATENT DOCUMENTS 9,298,020 B1 * 3/2016 Etzkorn ................. G02C 11/10
9,764,150 B2 * 9/2017 Loudin ................ A61N 1/3787
(Continued)

FOREIGN PATENT DOCUMENTS

CN 104334129 A 2/2015
CN 108290042 A 7/2018
(Continued)

OTHER PUBLICATIONS

International Searching Authority/European Patent Office, "Notification of Transmittal of the International Search Report and The Written Opinion of the International Searching Authority, or the Declaration," for PCT/US2021/044383, mailed Nov. 22, 2021, 17 pages.

*Primary Examiner* — Balram T Parbadia
*Assistant Examiner* — Gabriel A Sanz
(74) *Attorney, Agent, or Firm* — Haynes and Boone, LLP (57) ABSTRACT

In some aspects, an electronic contact lens for treating dry eye is presented. According to some aspects, the electronic contact lens includes a concave surface configured to conform to an eye of a patient, a sensor configured to generate a signal indicative of an eyelid movement, and at least one capacitor configured to store energy used for stimulating the eye. The electronic contact lens may further include at least two electrodes coupled to the at least one capacitor, wherein the at least two electrodes are exposed to the concave surface and configured to deliver power from the at least one capacitor to stimulate the eye. The electronic contact lens further includes a processor coupled to the sensor and electrodes. The processor may be configured to compute a blink rate from the sensor output, and, based on the blink rate, activate the at least two electrodes to stimulate the eye.

20 Claims, 5 Drawing Sheets

(51) Int. Cl.
*A61N 1/04* (2006.01)
*A61N 1/36* (2006.01)
*G02C 7/04* (2006.01)
*G02C 11/00* (2006.01)
*A61B 5/11* (2006.01)

(52) U.S. Cl.
CPC ....... *A61N 1/0404* (2013.01); *A61N 1/36046* (2013.01); *G02C 7/04* (2013.01); *G02C 11/10* (2013.01); *A61B 5/1103* (2013.01)

(58) Field of Classification Search
CPC .......... A61B 2560/0214; A61N 1/0404; A61N 1/36046; G02C 7/04; G02C 11/10
See application file for complete search history.

(56) References Cited

U.S. PATENT DOCUMENTS

| | | |
|---|---|---|
| 2012/0130398 A1 | 5/2012 | Ackermann et al. |
| 2013/0006326 A1 | 1/2013 | Ackermann et al. |
| 2014/0192312 A1 | 7/2014 | Pletcher et al. |
| 2014/0243971 A1* | 8/2014 | Pugh ........................ G02C 7/04 623/6.22 |
| 2017/0020390 A1* | 1/2017 | Flitsch ................... A61B 5/024 |
| 2018/0031867 A1 | 2/2018 | Lee et al. |
| 2018/0055448 A1* | 3/2018 | Karakaya ........... A61B 10/0012 |
| 2018/0136492 A1 | 5/2018 | An et al. |
| 2018/0161579 A1* | 6/2018 | Franke ................. A61B 5/1127 |
| 2018/0173011 A1 | 6/2018 | Barrows et al. |
| 2019/0344077 A1 | 11/2019 | Ackermann et al. |
| 2020/0196949 A1 | 6/2020 | Lee et al. |
| 2020/0306537 A1* | 10/2020 | Gutierrez ........... A61N 1/36034 |

FOREIGN PATENT DOCUMENTS

| | | |
|---|---|---|
| CN | 110366695 A | 10/2019 |
| EP | 3125021 A1 | 2/2017 |
| EP | 3255478 A1 | 12/2017 |
| WO | 2016065211 A1 | 4/2016 |

* cited by examiner

OPHTHALMIC DEVICES, SYSTEMS AND METHODS FOR TREATING DRY EYE

CROSS-REFERENCE TO RELATED APPLICATIONS

The present claims priority to and the benefit of U.S. Provisional Application No. 63/060,363, filed Aug. 3, 2020, the entirety of which is incorporated by reference.

TECHNICAL FIELD

The present disclosure relates generally to ophthalmic devices for treating dry eye, and, in particular but not exclusively, relates to smart contact lenses for treating dry eye by stimulating a surface of the eye.

BACKGROUND

"Dry eye" from contact lens wear may be understood as a catch-all term, as the root cause of eye dryness due to contact lens wear is multi-faceted. Many have been trying to address dry eye through contact lens materials innovations, such as increasing oxygen permeability, increasing hydrogel water content, changing the polymer formulation, and applying different surface coatings. In some subjects, hydrogels that seek to contain more water increase eye dryness, due to concentration differences in the fluids versus eye.

In many instances, the most comfortable eye environment for a contact lens wearer with dry eye (apart from not wearing the lenses at all), is when his or her eyes are closed, and the eyelids restore the thermal environment and tear film concentration levels due to evaporation.

The pathway for basal tear production is understood as mainly a closed loop thermal system. Studies have indicated that if a temperature difference is detected on the cornea due to natural tear film evaporation, the lacrimal gland produces tears to restore that thermal balance between the tear film and the corneal thermoreceptors. However, if there is sufficient dryness to cause mechanical discomfort but the lens still preserves the thermal environment (not triggering basal tear production), the dry eye condition may worsen. Accordingly, those who suffer from mild dry eye symptoms may dislike wearing contact lenses, as it aggravates or worsens their dry eye condition.

The symptoms may be temporarily mitigated through topical application of liquid medication in the form of various eye drops, for example. However, the temporary nature of the relief leads to repetitive use of the drops, which can be costly and inconvenient.

Thus, there remains a need for devices and/or techniques to treat dry eye conditions for contact lens wearers.

SUMMARY

Systems, devices and methods for treating dry eye are presented. In some aspects, an electronic contact lens for treating dry eye is presented. According to some aspects, the electronic contact lens includes a concave surface configured to conform to an eye of a patient, a sensor configured to generate a signal indicative of an eyelid movement, at least one capacitor configured to store energy used for stimulating the eye. The electronic contact lens may further include at least two electrodes coupled to the at least one capacitor, wherein the at least two electrodes are exposed to the concave surface and configured to deliver power from the at least one capacitor to stimulate the eye. According to some aspects, the electronic contact lens further includes a processor coupled to the sensor and the electrodes. The processor is configured to receive the signal from the sensor, determine when a blink occurs based on the signal, compute a blink rate from a set of two or more detected blinks, and, based on the blink rate, activate the at least two electrodes to stimulate the eye using a first stimulation amplitude.

In some aspects, the present disclosure describes a method of using a smart contact lens on an eye of a user. The smart contact lens includes a sensor configured to generate a signal indicative of an eyelid movement of the user, and at least two electrodes are configured to stimulate the eye. The method of using the smart contact lens includes repeatedly determining when a blink occurs based on the signal to generate a set of at least two detected blinks, computing a blink rate from the at least two detected blinks, and, based on the blink rate, determining whether to activate the at least two electrodes to stimulate the eye.

In some aspects, the present disclosure describes an ophthalmic device configured to conform to an eye of a user and overlap the cornea. The ophthalmic device includes a sensor configured to generate a signal indicative of a blink of the eyelid of the user, at least two electrodes configured to stimulate the eye, and a processor coupled to the sensor and the electrodes. The processor is configured to receive the signal from the sensor, estimate when a blink occurs based on the signal, compute a blink rate from a set of two or more detected blinks, and, based on the blink rate, activate the at least two electrodes to stimulate the eye sufficient to generate a blink reflex.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

The devices and methods described herein endeavor to supplement basal tear production (which may be hampered from contact lens wear or pre-existing mild dry eye disease) with reflex tearing. In some embodiments, reflex tearing is stimulated through neurostimulation of the eyeball (e.g., cornea or sclera) in the form of a contact lens to stimulate afferent neurons on the eyeball to produce reflex tearing through the lacrimal gland.

The contact lens form factor maintains refractive correction for visual acuity, and can also track blink rates, blink patterns, and/or blink detection, such that an algorithm may decide when and how often to stimulate the cornea. By detecting the blink fast enough, it is also possible to synchronize the stimulation during a blink, which can result in a more natural and user-friendly stimulation.

For many, dry eye disease is worsened due to low blink rates. This is especially a problem for young gamers or hyper-connected individuals, who forget to blink while playing video games or working. Accordingly, the stimulation strength may be increased (of course within safety limits) such that a contact lens may also serve as a "blink pacemaker," with a stimulation that is strong enough to suggest or trigger a blink in a user, thereby providing an additional means of dry eye treatment.

Figure 1:
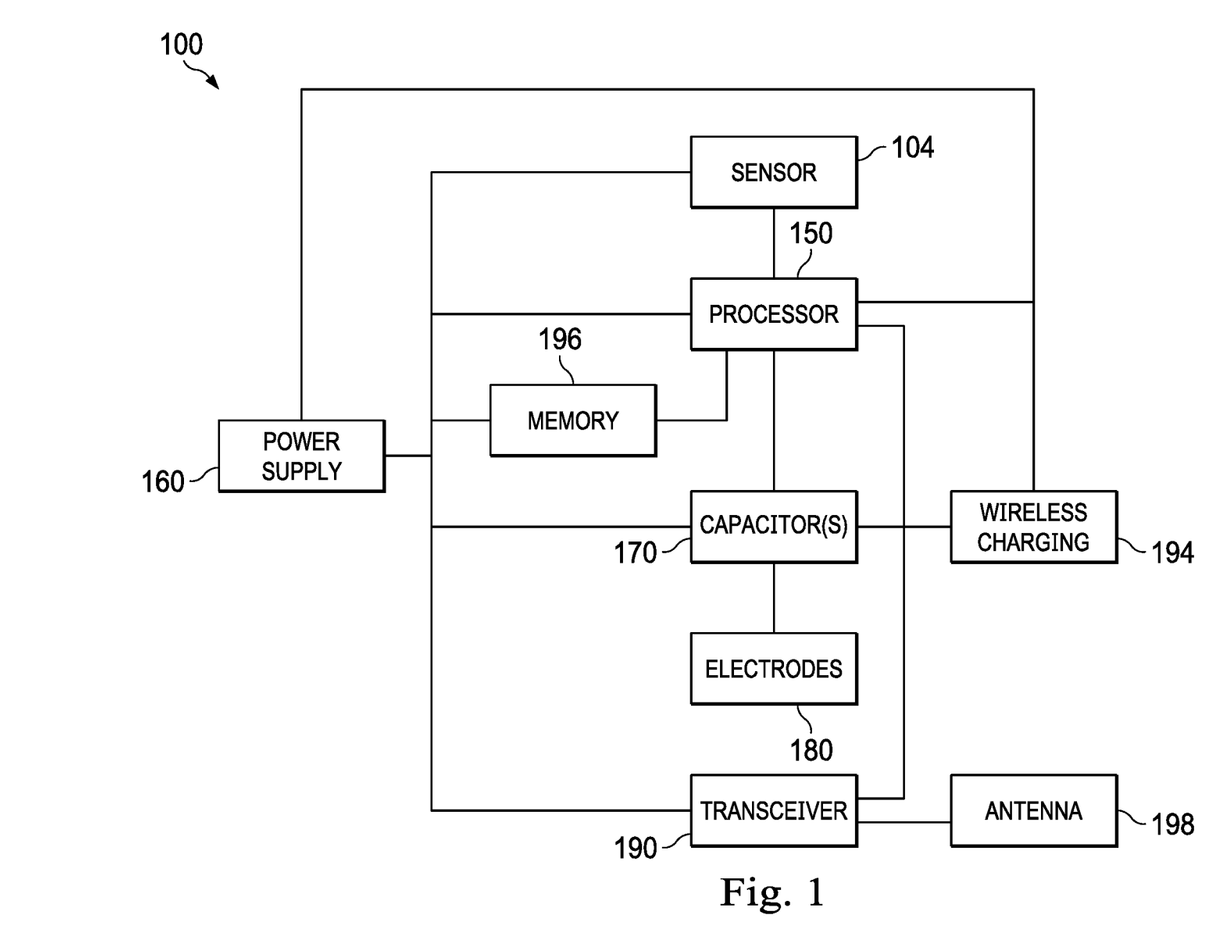
FIG. 1 is a block diagram of a smart contact lens, according to one embodiment.

FIG. 1 is a block diagram of electronic components of a smart contact lens 100, according to one embodiment. The contact lens 100 includes electronics/circuitry for treating dry eye while at the same time functioning as a traditional contact lens to provide vision correction to the user. As shown, the contact lens 100 includes at least one sensor 104 (or sensor(s)), a processor 150, a power supply 160, at least one capacitor 170 (or capacitor(s)), at least one pair of electrodes 180, a transceiver 190, a wireless charging device 194, a memory 196, and an antenna 198. Although the sensor 104 is referred to herein in the singular, it is understood that more than one sensor may be used.

The sensor 104 is configured to detect a blink of a user after the contact lens 100 is positioned on the user's eyeball. In at least one embodiment, the sensor 104 is an eyelid overlap sensor as described in U.S. Patent Publication 2018/0031867 by Shungneng Lee et al. and entitled "Device, System and Method for Detecting Overlap of an Ophthalmic Device by an Eyelid. Such a sensor 104 is also described further herein with respect to FIG. 2 below.

Contact lens 100 in FIG. 1 includes a power supply 160 in some embodiments. In some embodiments, the power supply includes an energy storage device, such as battery, which may be rechargeable. In some embodiments, the power supply 160 provides power to at least one of sensor 104, processor 150, transceiver 190 and memory 196. The power supply 160 may be configured to provide power to those components for long periods of time, such as several hours or an entire day.

Contact lens 100 in FIG. 1 includes a processor 150 in some embodiments. The processor 150 may take the form of any known processor, such as an integrated circuit (IC), an application-specific integrated circuit (ASIC), a field-programmable gate array (FPGA), or a general-purpose processor. The processor 150 is configured to provide any combination of the following: power management (such as managing the power supply 160 or energy harvesting view wireless charging), blink sensing, blink timing, or stimulating the blink reflex, according to an embodiment as discussed further herein.

The contact lens 100 in FIG. 1 includes capacitor(s) 170 and electrodes 180 in some embodiments. The capacitor(s) 170 provide a portion of the power to electrodes 180 during stimulation of the surface of the eyeball. The capacitor(s) 170 store electrical energy until needed for stimulation (delivered as electric energy per unit time, which is electric power), and the processor 150 controls the timing of the discharge of the capacitor(s) 170. The contact lens 100 may also include circuitry (not shown) that couples the capacitor(s) 170 to the electrodes 180 so that the electrodes provide a specific waveform, having a pulse amplitude (i.e., a voltage or current amplitude), pulse duration, pulse frequency, on time, off time, etc. as is known in the neurostimulation art. The capacitor(s) 170 deliver power to the electrodes 180 to deliver any known type of stimulation waveform. Capacitor(s) 170 may include two or more capacitors, such as supercapacitors, connected in series or parallel as needed to deliver appropriate amounts of power to the electrodes 180 for a given amount of time to stimulate the eye. In some embodiments, the power supply 160 recharges the capacitors 170 between discharges to keep them sufficiently charged to deliver power to the electrodes 180.

Contact lens 100 in FIG. 1 includes a transceiver 190 and an antenna 198 in some embodiments. The transceiver 190 may utilize any known type of communication protocols and waveforms for communicating with a device external to the user's body, such as a cell phone, smart phone, tablet computer or laptop computer. The transceiver 190 may utilize near-field communications (NFC), radio-frequency identification (RFID), or Bluetooth Low Energy (BLE) as examples. The transceiver 190 works together with antenna 198 to transmit or receive electromagnetic waveforms.

Contact lens 100 in FIG. 1 includes a memory 196 in some embodiments. The memory 196 is a semiconductor memory used to store data and/or instructions for other components. The memory 196 is any suitable semiconductor memory, such as a random-access memory (RAM) (such as a synchronous dynamic RAM or SDRAM), a read-only memory (ROM) (such as a programmable ROM or PROM), a flash memory or any combination thereof. The memory 196 may be used to store the instructions for operating processor 150, and/or transceiver 190. Thus, the contact lens 100 may include any combination of software and hardware utilizing a memory 196 and/or processor 150. At one extreme, the contact lens 100 may include no memory and the processor 150 is hard-wired to control the various components of the contact lens 100.

Contact lens 100 in FIG. 1 includes a wireless charging device 194 in some embodiments. An example wireless charging device 194 is an antenna, such as a loop antenna. The antenna generally can take any useful form for performing wireless charging via inductive wireless charging for the contact lens 100. The antenna may reside on a surface of, or may reside inside, the contact lens 100.

Many, or all, of the components shown in FIG. 1 are enclosed in a dielectric enclosure material (not shown). Thus, the contact lens 100 may be covered by an overmold, such as using a hydrogel or silicone hydrogel material, suitable for contacting surfaces of the eye and eyelids. The enclosure material includes at least some portion suitable for functioning as a traditional contact lens for providing vision correction to a user.

Figure 2:
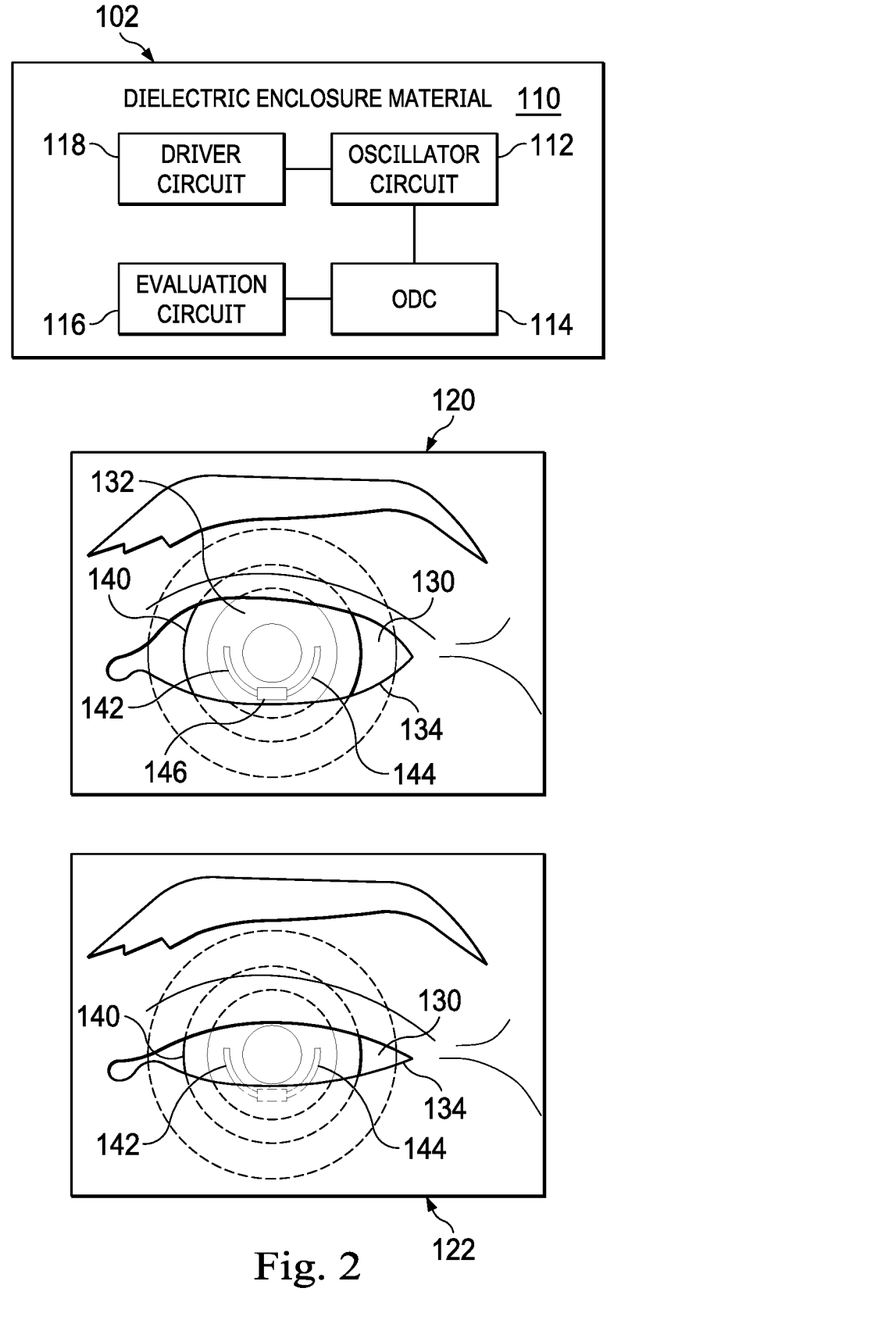
FIG. 2 is a block diagram of a sensor of a contact lens, according to one embodiment.

FIG. 2 presents a block diagram of an embodiment of components of sensor 104 of the contact lens 100 of FIG. 1. The sensor 104 includes circuitry to detect whether at least a portion of contact lens 100 is being overlapped by an eyelid of a user. Detection of this type of overlap (for brevity, referred to herein simply as "eyelid overlap") may be used, for example, in communications with a remote device, to evaluate a state of the user, to determine an operation to be performed by an accommodation actuator and/or the like. Additional details about such a sensor 104 are presented in U.S. Patent Publication 2018/0031867 and below.

Ophthalmic device 102 is one example of an embodiment comprising a lens (e.g., including the illustrative dielectric enclosure material 110) forming a sealed enclosure, wherein circuitry disposed in the sealed enclosure is operable to detect an amount by which an eyelid of a user overlaps ophthalmic device 102. Some or all the circuitry disposed in the sealed enclosure of the ophthalmic device 102 constitutes a sensor 104, according to at least one embodiment.

In the illustrative embodiment shown, such circuitry includes an oscillator circuit 112 comprising a first electrode portion and a second electrode portion (not shown) that variously extend along respective regions of ophthalmic device 102. The first electrode portion and the second electrode portion may be different respective portions of an inductive loop structure. Alternatively, the first electrode portion may be coupled to the second electrode portion via only one end of the first electrode portion. Oscillator circuit 112 may variously operate at different times under various conditions to facilitate eyelid overlap sensor functionality. For example, the first electrode portion and the second electrode portion may be configured to interact electromagnetically through the dielectric enclosure material 110— with an environment that is external to ophthalmic device 102. The environment may include some or all of a cornea of the user's eye, a tear film that adjoins the dielectric enclosure material 110 and, at times, some portion of an eyelid that might be overlapping ophthalmic device 102. In some embodiments, oscillator circuit 112 may be operated to induce an oscillation state with the first electrode portion and the second electrode portion.

For example, a driver circuit 118 of ophthalmic device 100 may also be disposed within the sealed enclosure. Driver circuit 118 may be coupled to drive oscillator circuit 112 with a signal that causes the first electrode portion and the second electrode portion to emit an electromagnetic field. Interaction between the electromagnetic field and an environment (not shown) external to the lens—e.g., the environment including a tear film on the lens and/or an eyelid of a user—may contribute to a signal oscillation state, or oscillation response, at oscillator circuit 112. The electromagnetic interaction may result in oscillator circuit 112 exhibiting one or more signal characteristics that are indicative of an amount of eyelid overlap. An oscillation detector circuit (ODC) 114, also disposed within the sealed enclosure, may be coupled to monitor for a threshold state of oscillation of oscillator circuit 112. As used herein, "threshold state of oscillation" refers to an oscillation response that results from a perturbation of a first state at the oscillator circuit, but where that first state is near an alternative second state wherein no such oscillation response would result from such perturbation.

In an embodiment, driver circuit 118 includes initialization circuitry (not shown) coupled to successively configure multiple initialization states of oscillator circuit 112. In such an embodiment, driver circuit 118 may further comprise a pulse generator (not shown) coupled to provide, for each of the multiple initialization states, a respective perturbation of the initialization state, wherein ODC 114 monitors oscillator circuit 112 to detect for any occurrence of a given oscillation response to the respective perturbation, ODC 114 may be coupled to determine one or more signal characteristics at oscillator circuit 112 e.g., wherein ODC 114 detects an amount of resistance that is provided, in part, by a tear film over ophthalmic device 100 and, at different times, a varying amount of resistance due to an eyelid that overlaps at least some part of ophthalmic device 100, Detecting the resistance may include detecting a threshold amount of current for starting up an oscillation with oscillator circuit 112 (wherein the threshold amount of input current changes depending at least in part on an amount of eyelid overlap).

ODC 114 may include or otherwise have access to memory resources (not shown) that store, for example, criteria information used to determine whether an output of oscillator circuit 112 qualifies as an oscillation response to a corresponding perturbation. Such criteria information may include a threshold minimum number of transitions by an output from oscillator circuit 112 within a defined time period. Alternatively, or in addition, criteria information may include a threshold minimum amplitude of the output from oscillator circuit 112. ODC 114 may monitor oscillator circuit 112 for the threshold state of oscillation based on the criteria information. For example, detecting for such an oscillation response may include ODIC 114 identifying whether an amplitude of an output by oscillator circuit is greater than (or equal to, in some embodiments) some threshold minimum amplitude. In another embodiment, detecting for an oscillation response includes ODC 114 counting transitions (e.g., through a threshold voltage or current level) by an output of oscillator circuit 112 during some predefined sample period. The total counted number of the transitions may then be compared to some predefined threshold minimum number of transitions for the output to qualify as an oscillation response.

An evaluation circuit 116 of ophthalmic device 100, disposed within the sealed enclosure, may be coupled to ODC 114 to receive an indication of the threshold state of oscillation and to correlate the indication of the threshold state of oscillation with an amount of eyelid overlap. For example, memory resources of ophthalmic device 100 may store reference information that corresponds to multiple initialization states (and/or corresponding oscillation responses) of oscillator circuit 112 each with a different respective amount of eyelid overlap. In such an embodiment, ODC 114 may communicate to evaluation circuit 116 an indication of a threshold initialization state for producing an oscillation response. Based on such an indication, evaluation circuit 116 may perform an evaluation—e.g., including a lookup of the reference information—to identify an amount of eyelid overlap that corresponds to the threshold initialization state. Evaluation circuit 116 may then generate one or more signals identifying the amount of eyelid overlap.

The threshold oscillation state of oscillator circuit 112 may change over time based on environmental conditions including, for example, an extent to which an eyelid of a user overlaps ophthalmic device 100. In one embodiment, ODC 114 successively performs multiple test rounds over time, each test round to detect a respective current threshold oscillation state of oscillator circuit 112, The test rounds may each include multiple sample cycles each corresponding to a different respective initialization state of oscillator circuit 112, For a given test round of the test rounds, the multiple sample cycles of the given test round may each correspond to a different respective value of an input to be provided to oscillator circuit 112 with driver circuit 118. For example, the input may include a current provided by the current source of driver circuit 118, in another embodiment, the input includes a voltage that biases oscillator circuit 112. The performance of a given test round may include dynamically selecting an initialization state (e.g., a level of an input) fear a sample cycle to be performed, wherein the selecting is based on a result of a preceding sample cycle and a binary search algorithm.

As shown in inset 120 of FIG. 1, one embodiment may include an ophthalmic device 140 (such as ophthalmic device 100) configured to be disposed in or on an eye 130 of a user—e.g, where ophthalmic device 140 is a contact lens to cover some or all of an iris 132 of eye 130. Movement of eye 130 and/or an eyelid 134 of the user may result in eyelid 134 overlapping ophthalmic device 140 by different amounts at different times. In an embodiment, ophthalmic device 140 includes a sensor mechanism to detect an amount of overlap by eyelid 134—e.g., based on a change of resistance that might result from any such overlap.

By way of illustration and not limitation, such a sensor mechanism may include a circuit (such as oscillator circuit 112) including a first electrode portion 142 and a second electrode portion 144 that variously extend in a light transmissive, dielectric enclosure material of ophthalmic device 140. Electrode portions 142, 144 may be configured to function as respective electrode portions each to interact electromagnetically with a tear film that extends over ophthalmic device 140 (e.g., where at least part of the tear film is between ophthalmic device 140 and eyelid 134), Electrode portions 142, 144 may function as electrode portions that variously extend each in a respective arc across at least some angular segment (e.g. at least 30°) of ophthalmic device 140—e.g., wherein such electrode portions connect to one another to form at least part of a loop structure of the same single electrode. The arcing electrode portions may be located near a periphery of ophthalmic device 140 (e.g., away from a center thereof) to mitigate interference with the user's viewing. For example, one or both of electrode portions 142, 144 may be located so that at least a portion of the electrode portions 142, 144 is closer to a periphery of ophthalmic device 140 than to a center of ophthalmic device 140.

In some embodiments, one or both of electrode portions 142, 144 are further configured to interact electromagnetically with another tear film that extends under ophthalmic device 140 (e.g., between eye 130 and ophthalmic device 140). As shown in inset 122, eyelid 134 and/or eye 140 may move over time, resulting in different amounts by which eyelid 134 overlaps one or both of electrode portions 142, 144. Different amounts of overlap by eyelid 134 may affect one or more signal characteristics associated with an electromagnetic interaction by electrode portions 142, 144 with the environment that is external to ophthalmic device 100.

Figure 3A:
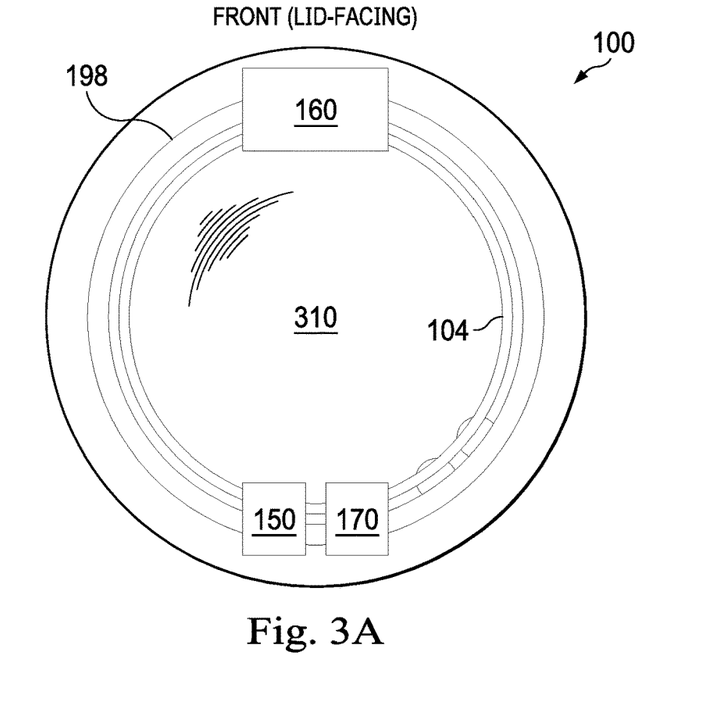
FIG. 3A is a view of a front/lid-facing/anterior side of a contact lens.
Figure 3B:
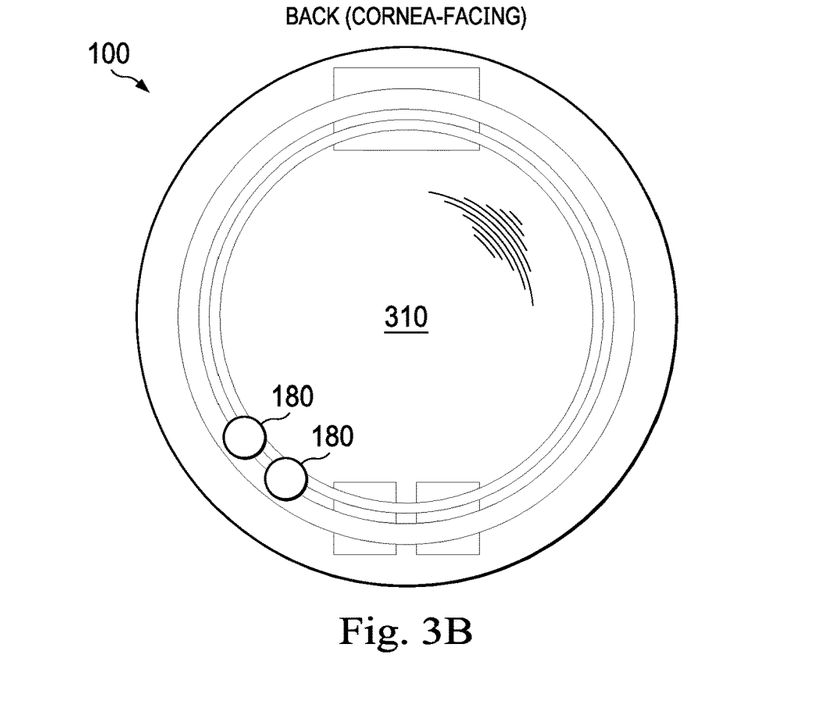
FIG. 3B is a view of a back/cornea-facing/posterior side of the contact lens, according to one embodiment.

In addition, although electrodes 142 and 144 are not illustrated in FIG. 2 to be part of a continuous conductor circumscribing the pupil, the electrodes 142 and 144 may instead be connected as part of a continuous conductor circumscribing the pupil, for example as illustrated in FIGS. 3A and 3B.

The processor 150 of FIG. 1 operates to determine an amount of eyelid overlap based on oscillation characteristics of a circuit structure (not shown) extending in enclosure 110. For example, processor 150 may provide functionality such as that of ODC 114 and/or evaluation circuit 116, and the sensor 104 may include the oscillator circuit 112 and the driver circuit 118. The sensor 104 and processor 150 may work together to provide blink detection. For example, if the extent of an eyelid of the user that the overlaps ophthalmic device 102 exceeds a threshold, as detected by the processor 150 based on outputs of the sensor 104, the processor determines that a blink has occurred.

FIGS. 3A and 3B present different views of a smart contact lens 100, according to one embodiment. More specifically, FIG. 3A presents a view of a front, or lid-facing, or anterior, side of the contact lens 100, and FIG. 3B presents a view of a back, or cornea-facing, or posterior, side of the contact lens 100. Although the drawings are two-dimensional, the back/cornea-facing surface of the contact lens is concave to conform to the eye, and the front/lid-facing surface is convex to conform to the corresponding eyelid, as is typical of contact lenses. Referring to FIGS. 3A and 3B, the contact lens 100 includes a processor 150, a battery 160, and one or more capacitors 170 (referred to herein as capacitor in the singular form). The contact lens 100 includes a radio frequency antenna 198 which can be used for communication or wireless charging or both.

The contact lens 100 includes a pair of electrodes 180. The electrodes 180 are used for stimulating a surface of the eye, such as a portion of the sclera or cornea. As shown, the electrodes 180 are positioned in or on the contact lens 100 so that an electrical stimulation can be delivered from the eyeball-facing side of the contact lens 100. As described previously, the capacitor 170 provides peak current support to the electrodes 180 during stimulation of the eye. When not stimulating, the electrodes 180 can be used to sense tear film quality of the tear film between the contact lens 100 and the eye. For example, the electrodes180 can be used to measure tear conductance or impedance, which is used as a measure of tear osmolarity, and the processor 150 may utilize a look-up table or formula to convert conductance measurements to osmolarity values. In an embodiment, the contact lens 100 uses measurements of blink rate and/or tear film values to determine when to generate a stimulation signal for electrodes 180.

The contact lens includes a sensor 104. The sensor 104 provides blink detection as described earlier. The sensor 104 is able to distinguish between tear film and an eyelid, according to an embodiment. For example, a tear film may be conductive of a current that is induced with the sensor circuit 104. The effect of such conductivity on operational characteristics of the sensor circuit may change over time with the changing external environment due to any additional conductance of a biological material (such as the eyelid) that comes in contact with the tear film. The extent to which an eyelid overlaps the sensor circuit may affect a resistivity of a current path that is in parallel with the tear film. In order to efficiently measure bio-conductance/bio-resistance of a tear film (in combination with that resulting from any eyelid overlap), some embodiments variously provide an inductive element that, for example, is coupled in parallel with an in-series combination of lens capacitance and a resistance of the tear film. During a resonance state of the sensor circuit, such an inductance element may cancel out or otherwise significantly offset an impedance provided with the lens capacitance. Therefore, at the resonance state of the sensor circuit, the frequency of oscillation may be automatically determined as a resonance for a combination of the inductor and the lens capacitance, effectively exposing a total amount of resistance provided by the tear film and eyelid (if present) e.g., where sensing of such resistance is not obscured by the impedance of the lens capacitance. This resistance may directly correlate with, and be sensed by determining, a minimum amount of current needed to startup oscillation of the sensor circuit.

Many or all the circuit components may be enclosed by dielectric enclosure material 310. The enclosure material, represented by the illustrative dielectric enclosure material 310, may function as a light transmissive lensing material and may form, at least in part, a sealed enclosure for circuitry of contact lens 100. The dielectric enclosure material 310 may be fabricated of a variety of materials compatible for direct contact with a human eye, such as a polymeric material, a hydrogel, PMMA, silicone based polymers (e.g., fluoro-silicon acrylate), or otherwise. The dielectric enclosure material 310 may be in the form of a round lens with a concave curvature configured to mount to a surface of an eye/eyeball.

Figure 3C:
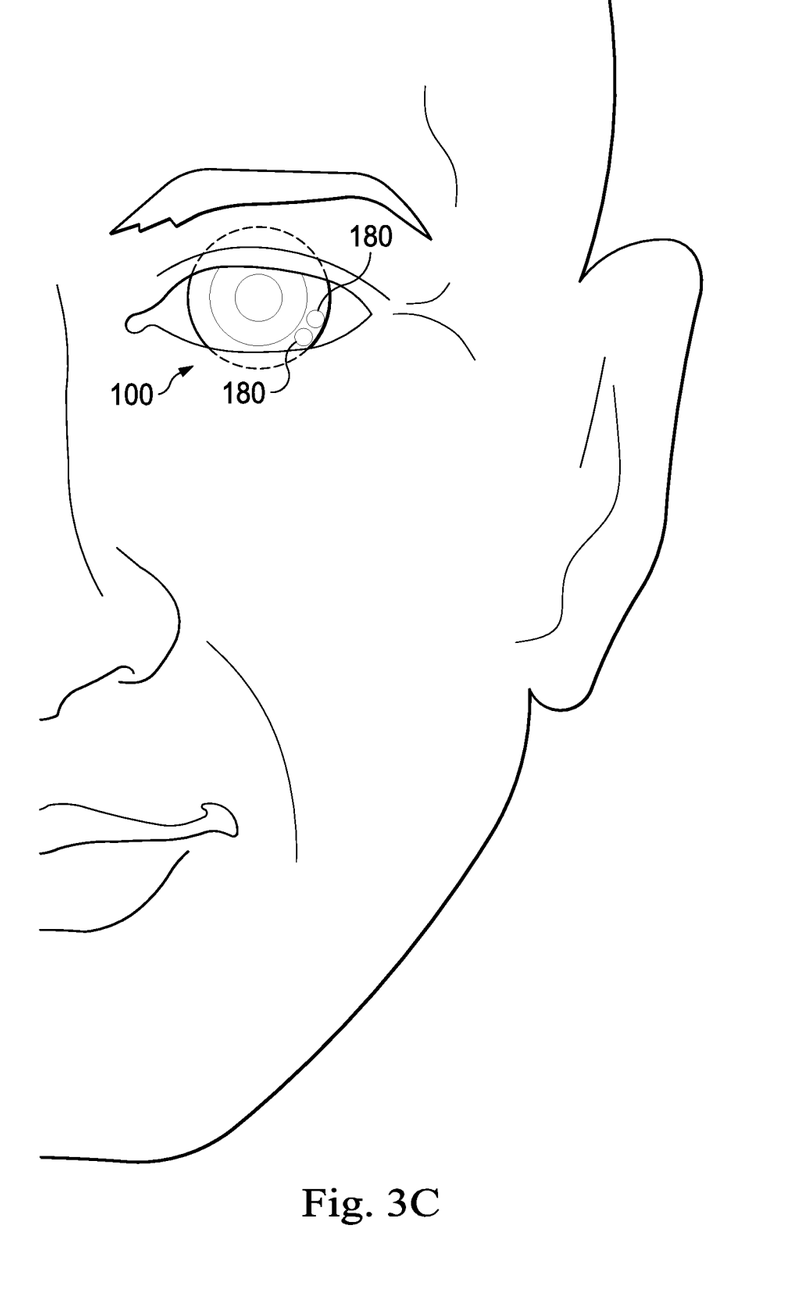
FIG. 3C is a view of the contact lens of FIGS. 3A and 3B in use in a user's eye, according to one embodiment.

FIG. 3C presents a view of the contact lens 100 of FIGS. 3A and 3B in use positioned on a user's eye (outer boundary of contact lens illustrated using dashed line). Only the electrodes of contact lens 100 are presented for illustrative purposes.

Figure 4:
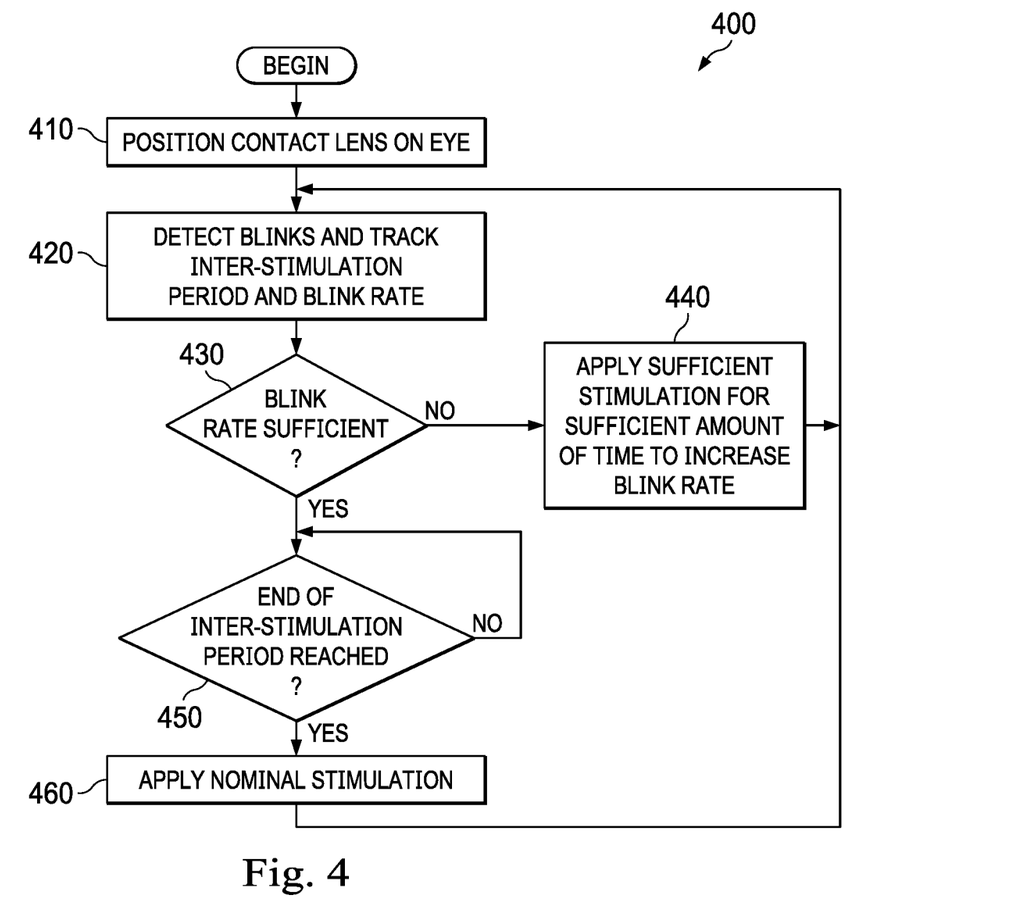
FIG. 4 illustrates a method of operating a contact lens, such as the contact lenses described herein, according to one embodiment.

FIG. 4 presents a method 400 of operating a contact lens, such as the contact lenses 100 described herein, according to one embodiment. The method 400 begins in step 410 with a user positioning a contact lens on the user's eye. Prior to placing the contact lens on the eye, the contact lens may be stored in a storage case that charges a power supply or other energy storage devices of the contact lens relied upon for operation.

Once the contact lens is placed on the eye, the user may have the option to calibrate nominal and increased stimulation amplitudes with a handheld device (not shown). For example, the contact lens may include electrodes for stimulating the eye, as described previously. A nominal stimulation amplitude can be used to stimulate the eye to generate reflex tears, e.g., providing a minor sensation to the user as if something is "in the eye," such as a speck of dirt. Reflex tears can be a form of basal tear replacement. An increased stimulation amplitude can be used to stimulate a blink reflex. The increased stimulation amplitude is generally larger than the nominal stimulation amplitude. The handheld device may communicate stimulation parameters to the contact lens via wireless communication. For example, the contact lens may include a transceiver and antenna as described previously.

Next in step 420 the contact lens detects blinks, e.g., using a sensor such as sensor 104 described previously, and tracks time between blinks to determine blink rate and also uses the time between blinks to determine whether a nominal stimulation should be applied as discussed below.

In step 430, the contact lens determines whether a blink rate (e.g., computed for a predetermined time period) is sufficient to provide dry eye relief or prevent or treat dry eye as the case may be. In one embodiment, the contact lens determines whether a blink rate is sufficient by comparing the blink rate to a threshold. The threshold may be patient-dependent or dependent on time of day or any of a number of other parameters. If the blink rate is not sufficient (e.g., is less than a threshold), the method transitions to step 440, wherein the contact lens applies a stimulation waveform using electrodes, such as electrodes 180 described herein. The stimulation waveform may use an increased stimulation, using a first current or voltage amplitude value, to trigger a blink reflex and increase stimulation rate. By applying a stimulation waveform with a certain regularity or periodicity over a set time period, the contact lens can function as a blink pacemaker to ensure that the blink rate is sufficient.

If, in step 430, the blink rate is determined to be sufficient, step 450 is performed next. In step 450, the contact lens determines whether an inter-stimulation period has been reached. When the inter-stimulation period is reached (e.g., the time since the last stimulation exceeds a threshold), a stimulation waveform is applied in step 460 using a nominal stimulation, using a second current or voltage amplitude value, supplied by the electrodes. In an embodiment, the nominal stimulation is high enough to result in reflex tearing but not high enough to generate reflex blinking. After a nominal stimulation is applied in step 460, the method 400 returns to step 420 and the process repeats. The process in method 400 repeats as long as the contact lens remains mounted on the eye. The user may remove the contact lens from the eye at any time, thereby ending method 400.

After the contact lens is removed from the eye, it may be returned to a case. Data may be collected by a contact lens during use, such as average blink rate for different time periods, tear osmolarity readings, data on how often stimulation was applied, etc.

Generally, any creation, storage, processing, and/or exchange of user data associated with the method, apparatus, and/or system disclosed herein is configured to comply with a variety of privacy settings and security protocols and prevailing data regulations, consistent with treating confidentiality and integrity of user data as an important matter. For example, the apparatus and/or the system, such as contact lens 100, may include a module that implements information security controls to comply with a number of standards and/or other agreements. In some embodiments, the module receives a privacy setting selection from the user and implements controls to comply with the selected privacy setting. In other embodiments, the module identifies data that is considered sensitive, encrypts data according to any appropriate and well-known method in the art, replaces sensitive data with codes to pseudonymize the data, and otherwise ensures compliance with selected privacy settings and data security requirements and regulations. Such as module may be implemented using processor 150, as an example, or a combination of processor 150 and a memory 196.

Persons skilled in the art will recognize that the devices, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An electronic contact lens for treating dry eye, the electronic contact lens comprising:
    a concave surface configured to conform to an eye of a patient;
    a sensor configured to generate a signal indicative of an eyelid movement;
    at least one capacitor configured to store energy used for stimulating the eye;

at least two electrodes coupled to the at least one capacitor, wherein the at least two electrodes are exposed to the concave surface and configured to deliver power from the at least one capacitor to stimulate the eye; and a processor coupled to the sensor and the electrodes, wherein the processor is configured to:
  receive the signal from the sensor;
  determine when a blink occurs based on the signal;
  compute a blink rate from a set of two or more detected blinks; and
  based on the blink rate, activate the at least two electrodes to stimulate the eye using a first stimulation amplitude.

2. The electronic contact lens of claim 1, wherein the processor is further configured to:
  determine whether an inter-stimulation period is exceeded since the last stimulation delivered from the at least two electrodes; and
  based on the determination, activate the at least two electrodes to stimulate the eye using a second stimulation amplitude.

3. The electronic contact lens of claim 2, wherein the first stimulation amplitude is larger than the second stimulation amplitude.

4. The electronic contact lens of claim 3, wherein the first stimulation amplitude is configured to stimulate a blink reflex, and wherein the second stimulation amplitude is configured to stimulate reflex tear production.

5. The electronic contact lens of claim 1, further comprising a power supply, wherein the power supply is coupled to the processor and configured to deliver power to the processor.

6. The electronic contact lens of claim 1, wherein the concave surface is configured to cover at least the cornea of the eye, and wherein the at least one capacitor, the sensor, and the processor are enclosed in an enclosure material suitable for contacting the eye and/or an eyelid.

7. The electronic contact lens of claim 6, wherein the electronic contact lens is configured to provide vision correction to the eye.

8. The electronic contact lens of claim 1, wherein the processor is further configured to activate the at least two electrodes to stimulate the eye with a frequency based on a target blink rate.

9. The electronic contact lens of claim 1, wherein the processor is further configured to:
  use the electrodes to measure a tear property; and
  activate the electrodes based on the tear property measurements.

10. The electronic contact lens of claim 1, wherein the sensor comprises:
  an oscillator circuit including a first electrode portion and a second electrode portion; and
  a driver circuit, the driver circuit coupled to drive the oscillator circuit with a second signal to cause the first electrode portion and the second electrode portion to emit an electromagnetic field that extends from the contact lens,
  wherein determining when a blink occurs based on the signal comprises:
    monitor the oscillator circuit for a threshold state of oscillation;
    determine an indication of the threshold state of oscillation; and
    correlate the indication of the threshold state of oscillation with a blink.

11. A method of using a smart contact lens on an eye of a user, wherein the smart contact lens comprises:
  a sensor configured to generate a signal indicative of an eyelid movement of the user; and
  at least two electrodes are configured to stimulate the eye, the method comprising:
    repeatedly determining when a blink occurs based on the signal to generate a set of at least two detected blinks;
    computing a blink rate from the at least two detected blinks; and
    based on the blink rate, determining whether to activate the at least two electrodes to stimulate the eye.

12. The method of claim 11, wherein the at least two electrodes stimulate the eye using a first amplitude if the blink rate is less than a first threshold, the method further comprising:
  determining that the blink rate exceeds the first threshold;
  determining that a time since the last delivered stimulation exceeds a second threshold; and
  based on determining that the first threshold is exceeded and that the second threshold is exceeded, activating the at least two electrodes using a second amplitude.

13. The method of claim 12, wherein the first amplitude is larger than the second amplitude, wherein the first amplitude is such that a blink reflex is stimulated, and wherein the second amplitude is such that a blink reflex is not stimulated.

14. The method of claim 11, wherein the first amplitude is selected to stimulate a blink reflex, and wherein the second amplitude is selected to stimulate reflex tear production.

15. The method of claim 11, wherein determining whether to activate the at least two electrodes to stimulate the eye comprises:
  determining that the blink rate is less than a threshold; and
  as a result of determining that the blink rate is less than a threshold, stimulating the eye using the electrodes.

16. An ophthalmic device configured to conform to an eye of a user and overlap the cornea, the ophthalmic device comprising:
  a sensor configured to generate a signal indicative of a blink of an eyelid of the user;
  at least two electrodes configured to stimulate the eye; and
  a processor coupled to the sensor and the electrodes, wherein the processor configured to:
    receive the signal from the sensor;
    estimate when a blink occurs based on the signal;
    compute a blink rate from a set of two or more detected blinks; and
    based on the blink rate, activate the at least two electrodes to stimulate the eye sufficient to generate a blink reflex.

17. The ophthalmic device of claim 16, further comprising:
  at least one capacitor coupled to the electrodes and configured to deliver power to the electrodes sufficient to generate the blink reflex.

18. The ophthalmic device of claim 17, further comprising:
  a battery coupled to the processor and configured to deliver power to the processor.

19. The ophthalmic device of claim 18, further comprising:
  a transceiver configured to communicate wirelessly with a first external device; and
  a wireless charging device configured to receive wireless power from a second external device to charge the battery; and a memory coupled to the processor and configured to store data on blink rate and stimulation delivered to the eye, wherein the processor is further configured to control the transceiver to communicate the stored data on blink rate and stimulation delivered to the eye to the first external device.

20. The ophthalmic device of claim 16, wherein the ophthalmic device is configured to provide vision correction to the user, and wherein the processor is further configured to:

keep track of an elapsed time since a previous stimulation is delivered; and if a computed blink rate exceeds a first threshold and the elapsed time exceeds a second threshold, activate the at least two electrodes to stimulate the eye sufficient to stimulate tear production but not a blink reflex.

* * * * *